United States Patent [19]
Gartside et al.

[11] Patent Number: 5,866,745
[45] Date of Patent: Feb. 2, 1999

[54] CATALYTIC/OXIDATIVE PROMOTED HYDROCARBON PYROLYSIS

[75] Inventors: Robert John Gartside, Summit; Atef M. Shaban, Manalapan, both of N.J.

[73] Assignee: ABB Lummus Global Inc., Bloomfield, N.J.

[21] Appl. No.: 13,399

[22] Filed: Jan. 26, 1998

[51] Int. Cl.$^6$ .............................. C07C 4/02; C07C 5/327; C10G 9/14

[52] U.S. Cl. ......................... 585/653; 585/651; 585/652; 585/654; 585/661; 208/130; 208/132

[58] Field of Search ................................... 585/651, 652, 585/653, 654, 661; 208/130, 132

[56] References Cited

PUBLICATIONS

Chen, Q., et al., "Oxidative Pyrolysis of Ethane", Ind. Eng. Chem. Res., vol. 36, No. 8, pp. 3248–3251, 1997.

Choudary, V.R., et al., "Coupling of Thermal Cracking with Noncatalytic Oxidative Conversion of Ethane to Ethylene", AIChE Journal, vol. 43, No. 6, pp. 1545–1550, Jun. 1997.

Choudary, V.R., et al., "Noncatalytic Oxypyrolysis of $C_{2+}$–Hydrocarbons from Natural Gas to Ethylene and Propylene in a Most Energy–Efficient and Safe Manner", Ind. Eng. Chem. Res., vol. 36, No. 6, pp. 2075–2079, 1997.

McCullough, J.P., et al., "Catalytic Dehydrogenation of Ethane by Selective Oxidation", Industrial and Engineering Chemistry, vol. 41, No. 2, pp. 1455–1459, Jul. 1949.

Layokun, S.K., "Oxidative Pyrolysis of Propane", Ind. Eng. Chem. Process Des. Dev., vol. 18, No. 2, pp. 241–245, 1979.

Joyce, J.H., et al., "Oxidation and Oxidation Dehydrogenation of Ethane and Propane", I & EC Process Design and Development, vol. 8, No. 1, pp. 17–25, Jan. 1969.

*Primary Examiner*—Glenn Caldarola
*Assistant Examiner*—In Suk Bullock
*Attorney, Agent, or Firm*—Alix, Yale & Ristas, LLP

[57] ABSTRACT

Light olefins are produced from a hydrocarbon feedstock by a steam pyrolysis reaction in the presence of small quantities of essentially pure oxygen and selected catalytic solids to enhance the steam pyrolysis reaction, to promote the combustion of hydrogen to water and to minimize the formation of carbon oxides. The catalysts are characterized by low surface area, by non-alumina supports and by the catalytic oxides of the group IVB, VB and VIB transition metals.

13 Claims, 1 Drawing Sheet

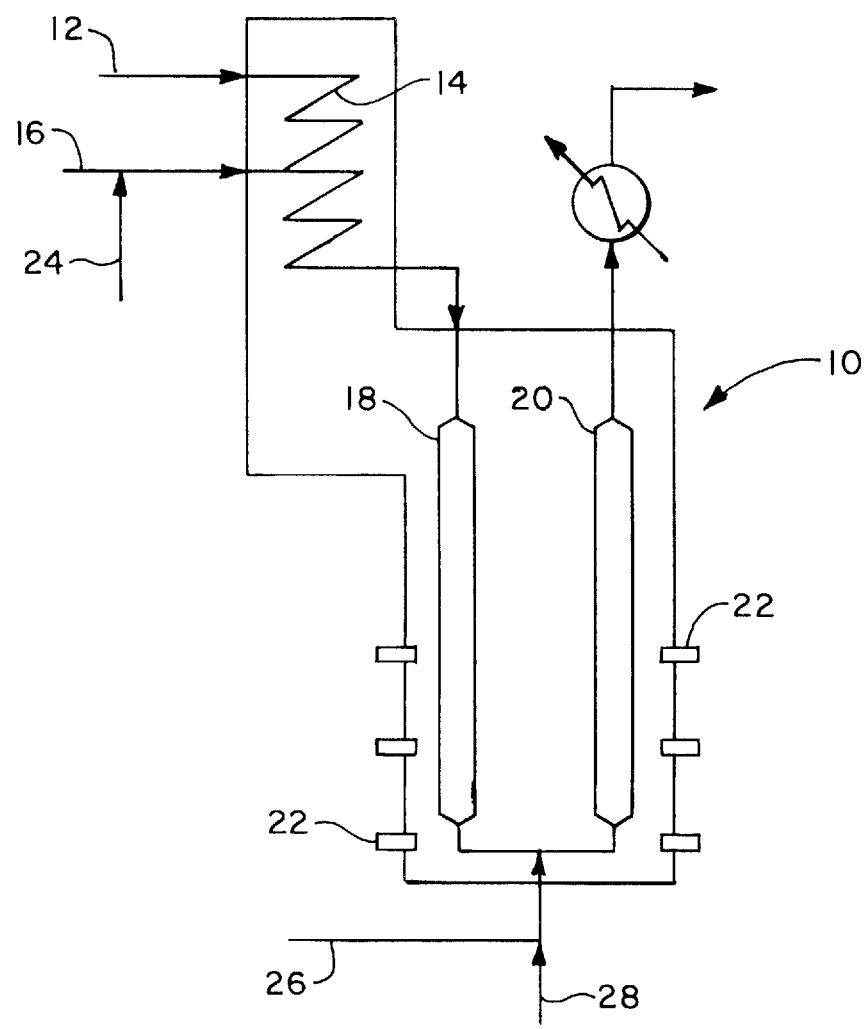

CATALYTIC/OXIDATIVE PROMOTED HYDROCARBON PYROLYSIS

BACKGROUND OF THE INVENTION

The present invention relates to the pyrolysis of hydrocarbons and particularly to the conversion of paraffins to olefins by a catalytic/oxidative promoted pyrolysis.

The steam cracking (pyrolysis) of hydrocarbons for the production of petrochemicals is almost exclusively carried out in tubular coils located in fired heaters. The pyrolysis section is considered the heart of an olefin plant and has the greatest influence on the economics of the overall plant.

The hydrocarbon feedstock may be any one of the wide variety of typical cracking feedstocks such as methane, ethane, propane, butane, mixtures of these gases, naphthas, gas oils, etc. The product stream contains a variety of components the concentration of which are dependent in part upon the feed selected. In the conventional pyrolysis process, vaporized feedstock is fed together with dilution steam to a tubular reactor located within a fired heater. The quantity of dilution steam required is dependent upon the feedstock selected; lighter feedstocks such as ethane require lower steam (0.2 lb./lb. feed), while heavier feedstocks such as naphtha and gas oils require steam/feed ratios of 0.5 to 1.0. The dilution steam has the dual function of lowering the hydrocarbon pressure and reducing the carburization rate of the pyrolysis coils.

In a typical pyrolysis process, the steam/feed mixture is preheated to a temperature just below the onset of the cracking reaction, typically 650° C. This preheat occurs in the convection section of the ethylene heater. The mix then passes to the radiant section where the pyrolysis reactions occur. Generally the residence time in the pyrolysis coil is in the range of 0.2 to 0.4 seconds and outlet temperatures for the reaction are on the order of 700° to 900° C. The reactions that result in the transformation of saturated hydrocarbons to olefins are highly endothermic thus requiring high levels of heat input. This heat input must occur at the elevated reaction temperatures. It is generally recognized in the industry that for most feedstocks, and especially for heavier feedstocks such as naphtha, shorter residence times will lead to higher selectivity to ethylene and propylene since secondary degradation reactions will be reduced. Further it is recognized that the lower the partial pressure of the hydrocarbon within the reaction environment, the higher the selectivity.

The flue gas temperatures in the radiant section of the fired heater are typically above 1,100° C. In a conventional design, approximately 32 to 40% of the heat fired as fuel into the heater is transferred into the coils in the radiant section. The balance of the heat is recovered in the convection section either as feed preheat or as steam generation. Given the limitation of small tube volume to achieve short residence times and the high temperatures of the process, heat transfer into the reaction tube is difficult. High heat fluxes (Q/A) are used and the operating tube metal temperatures are close to the mechanical limits for even exotic metallurgies. In most cases, tube metal temperatures limit the extent to which residence time can be reduced as a result of a combination of higher process temperatures required at the coil outlet and the reduced tube length (hence tube surface area) which results in higher flux and thus higher tube metal temperatures.

The product gas is sent to a closely connected transfer line exchanger where the temperature is rapidly reduced. This serves to prevent continued reaction which would reduce olefin yields. Following the exchangers, the product gas passes to a separation system. The gas is first cooled to essentially ambient conditions and condensable products removed. It is then compressed to a high pressure to enable separation of lighter products. Prior to separation, any $CO_2$ formed must be removed from the cracked effluent in order to avoid plugging and contamination problems in the downstream light olefins separation system. This is typically done using caustic scrubbing and the spent caustic must be neutralized prior to discharge to the environment. The other carbon oxide, CO, passes through the separation process but must be removed from the net hydrogen stream if that stream is to be utilized in hydrotreating units. Both of these operations have considerable capital and operating costs associated with them. In the normal pyrolysis process, carbon oxides are a result of the steam reforming reactions between the dilution steam and the hydrocarbon.

Dependent upon the feedstock, the light olefin separation system can be very complex and require a number of distillation towers. Further, the lower the molecular weight of the gas mixture, the higher the pressure and/or the lower the temperature has to be to achieve separation. The hydrogen content of the gas mixture is a key component in defining the molecular weight. The compression for both the product gas and the refrigeration systems represents a major capital and energy cost for the process. The lower the molecular weight, the greater the compression energy required. Thus high hydrogen concentration in the product gas impacts the process in two ways, increasing compression costs due to molecular weight and increasing refrigeration costs due to lower temperature requirements.

The use of oxygen in dehydrogenation processes has been considered in the past. In a typical oxy-dehydrogenation process, rather large quantities of oxygen are used at relatively low temperatures. In these processes, feed and oxygen are passed over a catalyst and reaction occurs. The oxygen quantities are typically high; on the order of 50% by volume or more of the hydrocarbon feed. These quantities are required since the oxy-dehydrogenation reaction is the only reaction occurring at the relatively low temperatures (300°–500° C.) involved. Thus to achieve commercially viable conversions, high oxygen is required. However, at high oxygen concentration, the reaction selectivity is low and high amounts of CO and $CO_2$ are formed over the mixed metallic oxide catalysts even at relatively low temperatures (300°–500° C.). Selectivity in this case is defined as the oxygen going to water compared to the oxygen resulting in carbon oxides. At these low temperatures, conversion is controlled by oxygen flow and in practice conversion must be limited to maintain high selectivity. These processes are thus generally uneconomic due to low conversion per pass (leading to high recycles), high levels of $CO_x$ formed, and the high cost of their removal. In addition, unlike the conventional process, relatively high concentration of co-product oxygenates are formed which are undesirable in the overall process. Thus in any pyrolysis operation that considers the use of oxygen, it is important that the $CO_x$ products be minimized. The oxygen should selectively react with the hydrogen to as high an extent as possible forming water as opposed to $CO_x$. The oxidative dehydrogenation reaction is net exothermic compared to the endothermic pyrolysis reaction. Heat removal places an additional limitation on conversion for oxydehydrogenation since, as temperature increases with the higher levels of oxygen required for conversion, selectivity decreases substantially.

The use of smaller quantities of oxygen at elevated temperatures (where pyrolysis reactions are significant) has been considered. See the article, "Oxidative Pyrolysis of Propane", Layokum, Stephan K., Ind Chem. Process Des. and Dev., vol 18, No. 2, 1979. In this case, small quantities of oxygen (2–3% of feed) were added to propane and reacted in an empty laboratory scale pyrolysis tube. Nitrogen was used as a diluent instead of steam. In that article, the authors report slight improvements in primary olefin selectivity (to propylene). Residence times were controlled at 0.1 seconds and reaction temperatures were 600°–700° C. No reference is made to $CO_x$ production or to the impact of such operation on ethylene furnaces and no catalyst was used.

Recently, there have been a number of literature articles that have addressed the use of oxygen for ethane pyrolysis. In all these cases, oxygen is added to the feedstock flow and passed through the reaction tube. No catalyst is involved. The authors discuss the reduction of the total fired energy of the system by utilizing the heat from the combustion reactions. In "Coupling of Thermal Cracking with Non-Catalytic Oxidative Conversion of Ethane to Ethylene", Choudary, V. R., et al., AIChE Journal, June 1997, vol 43, No. 6, the authors examine ethane pyrolysis with oxygen with limited oxygen (0 to 20%), no catalyst, and at low residence times and high temperatures (600°–850° C.). Their studies show substantial increases in $CO_x$ and substantial decreases in selectivity to ethylene as oxygen increases. Increasing oxygen from 0 to 10% by vol of feed increased selectivity to CO from 2% to 7%, selectivity to $CO_2$ from 0 to 0.3%, and decreased selectivity to ethylene from approximately 75 to 60%. In "Oxidative Pyrolysis of Ethane", Qi Chen et al, Ind Eng. Chem. Res, 1997, 36,3248–3251, the authors also use an empty laboratory scale pyrolysis tube with no catalyst and show that the addition of 7 vol % oxygen to ethane at constant process conditions increases selectivity to CO from essentially 0 to 5%, $CO_2$ selectivity increased to 0.3%, and ethylene selectivity decreased from 85 to 80%. The increased carbon oxide products formed in the non-catalytic processes have a definite negative effect on selectivity.

SUMMARY OF THE INVENTION

A process for the production of light olefins from feedstocks where small quantities of essentially pure oxygen are used in the presence of selected catalytic solids to enhance the rate of the steam pyrolysis reaction and selectively promote the combustion of hydrogen to water while minimizing the formation of carbon oxides, specifically carbon dioxide. The process is carried out at essentially conventional pyrolysis temperatures (700°–900° C.). The catalytic solids used result in very low production of $CO_x$ in the reaction to thus reduce selectivity losses of valuable olefinic products and also to minimize subsequent $CO_x$ removal costs from downstream processing. Further, the catalytic solids are formed into shapes or structures such that the pressure drop in the reactor is minimized. The selective combustion of hydrogen also has a dramatic impact on the downstream refrigeration costs associated with separation of hydrogen from lower olefins (ethylene).

BRIEF DESCRIPTION OF THE DRAWING

The drawing is a diagrammatic flow scheme illustrating the present invention.

DESCRIPTION OF THE PREFERRED EMBODIMENT

The present invention relates to the pyrolysis of hydrocarbons to produce olefins. The invention is particularly applicable to the pyrolysis of gaseous feeds such as ethane, propane, butane and isobutane and mixtures thereof, liquid feeds such as naphtha and gas oil, and could include other components such as methane and hydrogen.

The steam pyrolysis of hydrocarbons is normally carried out in tubular coils located in fired heaters. The pyrolysis temperatures are in the range of 700° to 900° C. with residence times in the pyrolysis coil ranging from 0.1 to 2.0 seconds. Free radical pyrolysis reactions occur and the product distribution will depend upon the feed but will typically have high concentrations of ethylene and methane with lesser amounts of propylene, butenes and higher products. Small quantities of CO are formed from the steam-hydrocarbon reforming reaction:

$$\text{Hydrocarbon} + \text{steam} \rightarrow CO + H_2$$

$CO_2$ is then formed from the $CO/CO_2$ equilibrium reaction. Reference may be had to U.S. Pat. No. 4,342,642 for a disclosure of a conventional type of pyrolysis heater. The pyrolysis reactions are highly endothermic thus requiring considerable heat input and waste heat recovery and the associated capital costs.

In accordance with the present invention, the pyrolysis is carried out with the addition of small quantities of oxygen. In the pyrolysis environment, the oxygen interacts with the feed to promote the production of primary olefins. First, the oxygen abstracts hydrogen from the feed to form $HO_2 \cdot$ radical and a feed radical as follows (using isobutane as an example):

$$C_4H_{10} + O_2 \rightarrow C_4H_9 \cdot + HO_2 \cdot$$

Additionally, the oxygen reacts with the feed radical that has been formed as follows:

$$C_4H_9 \cdot + O_2 \rightarrow C_4H_8 + HO_2 \cdot$$

Also, there are a number of reaction steps involving peroxides:

$$2HO_2 \cdot \rightarrow H_2O_2 + O_2$$

$$H_2O_2 + \text{surface} \rightarrow 2OH^{+1}$$

$$2HO_2 \cdot + \text{surface} \rightarrow H_2O + 3/2 O_2$$

The net result of these actions is the production of olefins and water. It is a further advantage of the system that water produced by this reaction acts as additional diluent and has in and of itself a positive effect on reaction selectivity by reducing the hydrocarbon partial pressure.

There are also the competing oxidation reactions to form CO and $CO_2$. These reactions are catalyzed by certain metals in the alloy steel pyrolysis tubes (such as Ni) but small quantities of sulfur can be used to poison their catalytic activity and reduce $CO_x$ formation. The reactions of oxygen to promote the production of primary olefins is enhanced by the presence of a free radical generating catalyst. It will work synergistically with the oxygen by abstracting hydrogen from the paraffin feed molecule thus forming primary radicals which are precursors for olefins and providing a source of more readily available hydrogen to react with the free oxygen. However, the free radical generating catalysts must also exhibit very low steam-hydrocarbon reforming activity. The steam-hydrocarbon reforming and combustion reactions are catalyzed by certain metal oxides such as nickel and iron (Group VIII metals), by catalysts with very high surface area, and by certain catalyst supports specifically alumina. Using solids with these characteristics will result in high $CO_x$ formation.

The solids in the present invention are limited to those characterized by the combination of low surface area, by non-alumina catalyst supports such as silica, pumice, or zirconium oxide, and by the catalytic oxides of the group IVB, VB, or VIB transition metals including vanadium, titanium, zirconium, or tungsten. These metals exhibit very high bonding energies with oxygen. This enhances hydrogen abstraction and allows the oxygen to react with the hydrogen selectively rather than react with the carbon containing free radical forming $CO_x$. These group IVB, VB, and VIB metals also are poor steam reforming catalysts; in fact many are known steam reforming catalyst poisons. Collectively, the solids which may be used in the present invention to promote the pyrolysis reactions while minimizing the production of carbon oxides are referred to herein as "promoted pyrolysis catalysts".

The promoted pyrolysis of the present invention is carried out in a typical pyrolysis heater at a temperature of 700° to 900° C. and with a residence time of 0.1 to 1.0 seconds. A portion of the pyrolysis tubes are filled with the promoted pyrolysis catalyst solids. The oxygen is introduced at concentrations below the flammability level of oxygen in the hydrocarbon and typically 1 to 10% by volume of the hydrocarbon. It is preferentially introduced admixed with the dilution steam or by a separate steam/oxygen injection line just prior to or intermediate within the pyrolysis zone.

The drawing illustrates a pyrolysis furnace 10 and the flow scheme for practicing the invention. Hydrocarbon 12, ranging from ethane through gas oil, enters the convection section 14 of the pyrolysis furnace 10 and is preheated to an intermediate temperature dependent upon its molecular weight. At that point, dilution steam 16 is added to the hydrocarbon flow and the mixture continues to pass through the convection section until a preheat temperature of the mixture reaches approximately 650° C. The mixture then enters the radiant pyrolysis tubes 18 and 20 and is rapidly heated by the burners 22 to temperatures ranging from 700° to 900° C. If oxygen is added to the steam at 24 prior to both of the radiant pyrolysis coils 18 and 20, then catalyst is located in reaction tube 18 or 20 or both. It is also possible to add the oxygen 26 at an intermediate point as the reaction is proceeding either with or without additional steam 28. In this case, reaction tube 18 acts as a conventional pyrolysis tube and some fraction of the total feed conversion occurs via conventional pyrolysis releasing hydrogen. The oxygen reacts with either the hydrogen present or the evolving hydrogen from the thermal dehydrogenation reactions (for example, ethane→ethylene+$H_2$) to release heat and form water. This heat reduces the net fired duty required for the reaction system. The catalyst located in the tubes is present in a form specifically designed to lower the pressure drop of the mixture passing through the tube.

There are a number of options for this concept. For example, oxygen could be added at both 24 and 26. Different quantities of catalyst could be employed in reaction tubes 18 and 20. Some portion of either reaction tube 18 or 20 could be located outside of the directly fired portion of the reaction system and utilize the heat from the exothermic oxidation reactions to provide the endothermic heat of pyrolysis. All of these options are within the spirit of the concept.

In a typical pyrolysis fired heater, the reaction heat is normally provided at 35 to 40% efficiency. As previously indicated, this requires considerable waste heat recovery in a convection section to reach economical heat recovery levels. In the present invention where there is in situ heat produced via the net hydrogen/oxygen combustion within the pyrolysis tube itself, this portion of the reaction heat is provided at 100% efficiency. This reduces the requirement to provide the endothermic heat of reaction by radiant heat transfer from the firebox. Thus, for every unit of heat provided via oxygen addition, there is a reduction of 2.5 to 3 units of fired heat duty.

In order to obtain relatively short residence times within the pyrolysis tube, it is desirable to use very high gas velocities. It is also important that the pyrolysis tube have sufficient surface area to allow for the necessary heat transfer from the radiant firebox through the tube walls to the reaction mixture. High velocities maximize the length of a coil for a given residence time thus maximizing surface and minimizing flux. The required heat flux for the reaction is defined by the total of the sensible and endothermic reaction heat for the reaction mixture flowing through the coil divided by the surface area of the coil. Further, the free radical reaction chemistry for olefin production is favored by low pressures. Thus the design of a pyrolysis coil is a balance between the desire for short residence time, requiring high velocity and short linear distances, and the necessity to avoid very high tube temperatures created by high heat flux. If heat is generated "in situ" as is done in promoted pyrolysis, this will reduce the required flux for a given pyrolysis coil. Reduced flux can be capitalized upon by an increase in reaction run length, by increased coil capacity, or by decreased residence time leading to increased reaction selectivity. This is especially true for liquid feeds.

The presence of solids (catalyst) within the pyrolysis coil will create additional pressure drop and increase overall reaction pressure. This will have a negative impact on pyrolysis reaction selectivity. Further, since the maintenance of high gas velocities are important for heat management control, it is essential that the catalyst be in a form that reduces the pressure drop within the coil. The preferred forms of the promoted pyrolysis catalyst are catalyst structures that are fixed or unitary and that minimize pressure drop. Such catalyst structures may include the catalyst in the form of a metal oxide gauze, wire mesh or screen, the catalyst in the form of a coated three dimensional structure or the catalyst in the form of catalyst particles fixed into a wire fiber mesh. These structures, generally referred to herein as unitary catalyst structures (as opposed to unconfined granular catalyst particles), are characterized by higher voidage fractions than typical packed catalyst beds. The higher voidage fraction provides a lower pressure drop which is particularly advantageous in the present invention. When catalytic solids are present, they decrease the free area available in the coil for gas flow and thus increase pressure drop. At the velocities normally found in pyrolysis coils (>150 meters/sec), the pressure drop through the coil increases rapidly with even small reductions in free area. The outlet pressure of the coil is fixed by the separation system, hence any increase in coil pressure drop increases the absolute pressure required at the coil inlet. Higher pressures upstream of the coil impact the ability to vaporize liquid feedstocks. The design solution to increased pressure drop is to increase coil diameter (to give the same free area with solids as the smaller empty tube). As tube diameter increases, the ability to transfer heat into the center of the tube is impacted. Non uniform temperature profile over the tube radius results in selectivity losses. It is thus desirable to have high voidage solids. Typical empty coil pressure drops are on the order of 20 psi. An unconfined solid could increase this to a pressure drop of 50 psi or greater. With the proper choice of unitary solids, pressure drops can be no more than 20% greater than the equivalent empty tube at the same diameter. Maintaining the same diameter allows the designer to maintain the equivalent heater design and heat transfer characteristics within the reaction tube.

EXAMPLES

Example 1

Conventional Pyrolysis of Isobutane

Isobutane was fed to a laboratory reactor with a net residence time of 0.59 seconds and at a temperature of 790° C. The pyrolysis tube was empty (no catalyst) and a conversion of 60% was achieved. The isobutylene yield was 16.3%, the propylene yield was 1.05%, the CO yield was 0.4% and the $CO_2$ yield was nil. The CO and $CO_2$ yields are expressed on a carbon basis. They are higher on a full molecular weight basis. Steam was used as a diluent.

Example 2

Pyrolysis of Isobutane with Oxygen—No Catalyst

The case of example 1 was repeated but with the addition of 4.4 vol % $O_2$ in the feed. At the same 60% conversion, the isobutylene yield remained the same at 17.1%, the hydrogen yield was 0.9%, the propylene yield was 17.1%. However, the CO yield had increased to 1.1% and the $CO_2$ yield to 0.2%. Oxygen had decreased hydrogen but impacted CO and $CO_2$ yields.

Example 3

Pyrolysis of Isobutane with Oxygen—Vanadia on Pumice Catalyst, $TiO_2$ on Silica Catalyst The conditions of example 2 were repeated with vanadia catalyst present. At the same 60% conversion, the yield of isobutylene has increased to 18.75%, the propylene yield was 17.1%, the hydrogen yield was 0.9%, CO yield was 0.5% and the $CO_2$ yield was 0.05%. Similarly for the Ti catalyst, the isobutylene yield was 19.5%, the hydrogen 0.9%, the propylene was 17.1%, the CO was 0.1% and the $CO_2$ yield was 0.05%.

The presence of the "promoted pyrolysis" catalyst dramatically increased primary olefin yield and suppressed the formation of CO and $CO_2$ relative to the non-catalytic case with the same oxygen addition.

Example 4

Pyrolysis of Isobutane Without Oxygen—Pt on Alumina Catalyst

The conditions of example 1 were repeated but in the presence of a catalyst consisting of platinum on an alpha alumina support. At the same 60% conversion of isobutane, the isobutylene yield had increased to 18.75%, the propylene yield was 17.1%, the hydrogen yield was 2.4%, the CO yield was 1.4% and the $CO_2$ yield was 0.85%. Clearly, while the catalyst had a beneficial effect on the primary olefin yield, the catalyst with alumina support and metal from Group VIII had dramatically increased the reforming reactions leading to much higher hydrogen, carbon monoxide, and carbon dioxide. This has negative economic implications for the ethylene process.

Example 5

Pyrolysis of Isobutane with Oxygen—Pt on Alumina Catalyst

The conditions of example 4 were repeated using 7% by volume oxygen. In this case at 60% conversion, isobutylene yield was 17.5%, propylene was 15.1%, hydrogen was 4.4%, CO was 3.2% and $CO_2$ was 1.5%. Clearly, once oxygen is introduced over this type of catalyst, the results are negative. Platinum is a group VIII noble metal known to promote reforming and combustion reactions.

Example 6

Pyrolysis of Naphtha without Oxygen—Various Catalysts

In another laboratory test unit, naphtha was pyrolyzed over various catalysts at identical steam/hydrocarbon ratios (0.7 by weight) and temperature profile and residence times. At a methane yield of 15%, representing constant conversion, the CO was measured as indicative of reforming reactivity. The following table compares CO yield with different catalysts:

| Catalyst | CO Yield, wt % feed (as CO) |
| --- | --- |
| None | 0.15% |
| Magnesium oxide support (no metal catalyst) | 0.70% |
| V on pumice | 0.20% |
| Silica support (no metal catalyst) | 0.18% |

This clearly demonstrates that a MgO catalyst support catalyzes reforming reactions while a silica support does not. Further, there is minimal increase with the pumice support.

Example 7

Conventional and Catalytic Pyrolysis of Ethane

Ethane was pyrolyzed in a laboratory reactor with no solids present and in the presence of various combinations of oxygen and/or catalyst. The results are presented in the Table below at a conversion of ethane with 0.3 wt steam dilution of 70%.

| Case | $C_2H_4$ | $H_2$ | $CH_4$ | CO | $CO_2$ |
| --- | --- | --- | --- | --- | --- |
| Pyrolysis only | 55.0 | 4.1 | 3.5 | 0.15 | 0.05 |
| Pyrolysis + 3.5% $O_2$ | 55.0 | 3.9 | 4.2 | 1.3 | 0.15 |
| 4.0% $O_2$ + V on pumice catalyst | 55.0 | 3.9 | 3.5 | 0.6 | 0.05 |
| No $O_2$ + high surface area alumina catalyst support | 23.0 | 5.5 | 9.2 | 2.0 | ~3 |
| Li/La oxide catalyst + 6.6% $O_2$ | 34.0 | 3 | 5.5 | 3.2 | 0.4 |

These results for ethane show the detrimental effects of high surface area alumina catalyst supports and the use of Li/La metal oxides (group I and III alkali metals). It also reaffirms the benefits of the "promoted pyrolysis" type catalysts (V on pumice) with oxygen on reduced CO and $CO_2$ yields compared to the use of oxygen alone.

We claim:

1. A process for the pyrolysis of hydrocarbons to produce olefins comprising passing a mixture of a hydrocarbon and steam in a ratio of from 0.2:1 to 1.5:1 parts steam to hydrocarbon by weight and oxygen in an amount of from 1 to 10% of the hydrocarbon by volume through a reaction system containing a catalyst having a surface area of less than 20 m² per gram and containing a group IVB, VB or VIB transition metal oxide component and maintaining said reaction system at a temperature between 700° C. and 900° C.

2. A process as recited in claim 1 wherein said step of passing said mixture through a reaction system comprises passing said mixture through a pyrolysis tube.

3. A process as recited in claim 1 wherein said catalyst is titanium oxide on silica.

4. A process as recited in claim 1 wherein said catalyst is vanadium oxide on pumice.

5. A process as recited in claim 1 wherein said catalyst contains said group IVB, VB, or VIB transition metal oxide component on non-alumina support.

6. A process as recited in claim 1 wherein said hydrocarbon is selected from the group consisting of ethane, propane, butane and mixtures thereof.

7. A process as recited in claim 1 wherein said hydrocarbon is naphtha.

8. A process as recited in claim 1 wherein said oxygen is first admixed with at least a portion of said steam and then said admixture is mixed with said hydrocarbon.

9. A process as recited in claim 8 wherein said admixture is mixed with a mixture of said hydrocarbon and steam.

10. A process as recited in claim 8 wherein said admixture is introduced into said hydrocarbon prior to passing said mixture into said reaction system.

11. A process as recited in claim 8 wherein said hydrocarbon is partially reacted prior to mixing said admixture with said hydrocarbon.

12. A process as recited in claim 1 wherein the outlet pressure from said reaction system is less than 50 psig.

13. A process as recited in claim 1 wherein said catalyst contained in said reaction system comprises unitary catalyst structures providing low pressure drop through said catalyst.

* * * * *